United States Patent

Platzek et al.

[11] Patent Number: 5,980,864
[45] Date of Patent: Nov. 9, 1999

[54] 1,4,7,10-TETRAAZACYCLODODECANE BUTYLTRIOLS, PROCESSES FOR THEIR PRODUCTION AND PHARMACEUTICAL AGENTS CONTAINING THEM

[75] Inventors: Johannes Platzek; Heinz Gries; Hanns-Joachim Weinmann; Gabriele Schuhmann-Giampieri; Wolf-Rüdiger Press, all of Berlin, Germany

[73] Assignee: Schering Aktiengellsellschaft, Berlin, Germany

[21] Appl. No.: 07/671,041

[22] Filed: Mar. 19, 1991

[30] Foreign Application Priority Data

Mar. 19, 1990 [DE] Germany ............... 40 09 119

[51] Int. Cl.$^6$ ............... A61B 5/055
[52] U.S. Cl. ............... 424/9.363; 534/16; 540/465; 540/474; 514/184; 514/836
[58] Field of Search ............... 424/1.1, 9.363; 534/14, 15, 16; 540/465, 474; 514/184, 836; 436/173; 600/420

[56] References Cited

U.S. PATENT DOCUMENTS

| | | | |
|---|---|---|---|
| 4,062,934 | 12/1977 | Tilly et al. | 424/5 |
| 4,284,620 | 8/1981 | Lin et al. | 424/5 |
| 4,439,613 | 3/1984 | Sovak et al. | 549/347 |
| 4,547,357 | 10/1985 | Pfeiffer et al. | 424/6 |
| 4,885,363 | 12/1989 | Tweedle et al. | 540/465 |
| 5,059,412 | 10/1991 | Simon et al. | 424/1.1 |
| 5,358,704 | 10/1994 | Tweedle et al. | 424/9.363 |
| 5,474,756 | 12/1995 | Tweedle et al. | 424/9.363 |
| 5,674,470 | 10/1997 | Tweedle et al. | 424/9.363 |

FOREIGN PATENT DOCUMENTS

| | | |
|---|---|---|
| 604249 | 7/1987 | Australia . |
| 255471 | 2/1988 | European Pat. Off. . |

*Primary Examiner*—Gary E. Hollinden
*Attorney, Agent, or Firm*—Millen, White, Zelano & Branigan P.C.

[57] ABSTRACT

1,4,7,10-Tetraazacyclodedecane butyltriols of general formula $I_A$

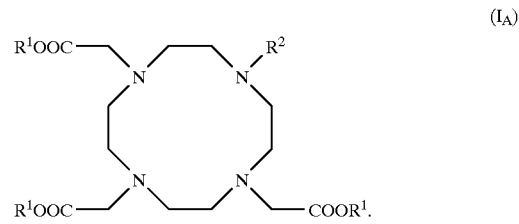

in which $R^1$ means hydrogen or a metal ion equivalent independent of one another and $R^2$ means a butyltriol radical as well as their salts with organic or inorganic bases or amino acids are valuable pharmaceutical agents.

12 Claims, No Drawings

1,4,7,10-TETRAAZACYCLODODECANE BUTYLTRIOLS, PROCESSES FOR THEIR PRODUCTION AND PHARMACEUTICAL AGENTS CONTAINING THEM

BACKGROUND OF THE INVENTION

This invention relates to 1,4,7,10-tetraazacyclodedecane butyltriols, their complexes and complex salts, agents containing these compounds, their use as diagnostic agents and therapeutic agents as well as processes for the production of these compounds and agents.

In European patent application 87730085.5 with the publication number 0 255 471 macrocyclic compounds of general formula I

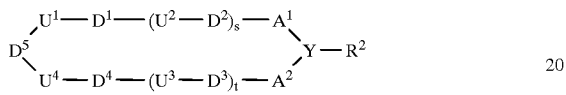

(I)

are claimed,
in which
- Y is a nitrogen atom or phosphorus atom,
- $A^1$ and $A^2$ are the same or different and each is a straight-chain or branched alkylene group with 2 to 6 carbon atoms,
- $U^1$, $U^2$, $U^3$, $U^4$ are the same or different and each is a direct bond or a straight-chain or branched alkylene group with 1 to 6 carbon atoms,
- $D^1$, $D^2$, $D^3$, $D^4$ are the same or different and each is an oxygen atom or sulfur atom, an alkylene group with 1 to 6 carbon atoms or a group $N-R^7$ with $R^7$ meaning a hydrogen atom, a straight-chain or branched alkylene chain with 1 to 4 carbon atoms, which on the end carries a $COOR^1$ group, and $R^1$ stands for a hydrogen atom or a metal ion equivalent.
- $D^5$ has the meaning indicated for $D^1$, $D^2$, $D^3$ and $D^4$ as well as the group

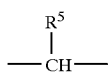

with $R^5$ meaning a hydrogen atom or a straight-chain or branched saturated or unsaturated $C_1$–$C_{20}$ alkylene group, optionally substituted by hydroxy, mercapto, imino and/or amino group(s), optionally containing imino, phenylenoxy, phenylenimino, amide, ester group(s), oxygen atom(s), sulfur atom(s) and/or nitrogen atom(s), which on the end exhibits either a functional group or a macromolecule B bound by it,
- s and t represent whole numbers from 0 to 5,
- $R^2$ represents hydrogen, a straight or branched, saturated or unsaturated alkyl, acyl or acylalkyl group with 1 to 16 carbon atoms optionally substituted by one or more hydroxy or lower alkoxy groups,
- $-CH_2-X-V$ with X meaning carbonyl, a straight-chain or branched-chain alkylene group with 0 to 10 carbon atoms, which optionally is substituted by one or more hydroxy or lower alkoxy groups or a straight-chain or branched-chain alkylene group interrupted by oxygen atoms with 2 to 23 hydrocarbon atoms, V meaning

of $-COOR^6$, and $R^3$ and $R^4$, independently independently of one another, represent hydrogen, a straight or branched alkyl group with 1 to 16 carbon atoms optionally substituted by one or more hydroxy or lower alkoxy groups or $R^3$ and $R^4$ together with the nitrogen atom represent a saturated, five or six ring optionally containing another heteroatom and $R^6$ represents hydrogen or a saturated, unsaturated straight-chain or branched-chain or cyclic hydrocarbon radical with up to 16 carbon atoms or an aryl or aralkyl group, or $R^2$ or $R^3$ represent a second macrocycle of formula I'—bound by an alkylene chain (K) containing 2 to 20 carbon atoms, which optionally carries carbonyl groups on the ends and optionally is interrupted by one or more oxygen atoms or $R^1$ carboxymethylimino groups or is substituted by one or more hydroxy, lower alkoxy or carboxy lower alkyl groups—

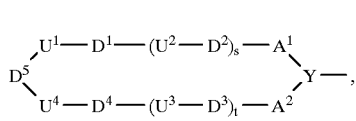

(I')

which can be of a different structure than the parent substance of the first, or $R^2$ means B or $CH_2-COB$, provided that, if $R^2$ stands for B or $CH_2-COB$, $R^5$ means a hydrogen atom, that at least two $COOR^1$ groups are present in the molecule and that two heteroatoms of the macrocycle are each connected by an alkylene group with at least two carbon atoms, and functional groups existing in the molecule optionally are conjugated with macromolecules and optionally free carboxyl groups are made into salts with organic or inorganic bases or amino acids and basic groups with inorganic or organic acids.

The substances and the solutions prepared from them meet the demands to be made of pharmaceutically usable chelates. They have a strong and adaptable effectiveness, by the selection of suitable metal atoms, on the respective principles of the diagnostic or therapeutic method (x ray, NMR, ultrasound, nuclear medicine).

SUMMARY OF THE INVENTION

Of the many compounds in EP-A- 0 255 471, the 1,4,7, 10-tetraazacyclodedecane butyltriols of general formula $I_A$

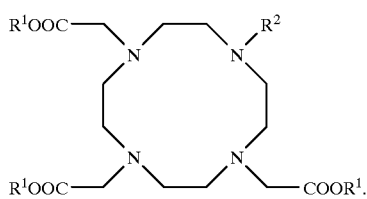

(I_A)

in which
- $R^1$ means hydrogen or a metal ion equivalent independent of one another and
- $R^2$ means a butyltriol radical as well as their salts with organic or inorganic bases or amino acids, exhibit such outstanding properties that even in comparison with the structurally very closely related compound disclosed in EP-A 0 255 471 (Example 6), the use of these selected compounds guarantees a substantial advantage.

Compounds of general formula $I_A$ with $R^1$ meaning hydrogen are designated as complexing agents and with at least two of substituents $R^1$ meaning a metal ion equivalent are designated as metal complexes.

The element, which forms the central ion of the physiologically compatible complex salt, can, of course, also be radioactive for desired purpose of use of the diagnostic medium according to the invention.

If the medium according to the invention is intended for use in NMR diagnosis, the central ion of the complex salt has to be paramagnetic. This involves especially the bivalent and trivalent ions of the elements of the atomics numbers 21–29, 42, 44 and 58–70. Suitable ions are, for example, the chromium(III), manganese(II), iron(II), cobalt(II), nickel (II), copper(II), praseodymium(III), neodymium(III), samarium(III) and ytterbium(III) ion. Because of their very strong magnetic moment there are especially preferred the gadolinium(III), terbium(III), dysprosium(III), holmium (III), erbium(III) or iron(III) ion.

For use of the media according to the invention in nuclear medicine the central ion has to be radioactive. For example, radioisotopes of the elements copper, cobalt, gallium, germanium, yttrium, strontium, technetium, indium, ytterbium, gadolinium, samarium and iridium are suitable.

If the medium according to the invention is intended for use in x-ray diagnosis, the central ion has to be derived from an element of higher atomic number to achieve a sufficient absorption of the x rays. It was found that for this purpose diagnostic media, which contain a physiologically compatible complex salt with central ions of elements of the atomic numbers between 21–29, 42, 44, 57–83, are suitable; they are, for example, the lanthanum(III) ion and the above-named ions of the lanthanide series.

Preferred radicals $R^2$ are 2,3,4-trihydroxybutyl- and the 1-hydroxymethyl-2,3-dihydroxypropyl radical.

If not all acidic hydrogen atoms are substituted by the central ion, one, several or all remaining hydrogen atom(s) can be replaced by cations of inorganic and/or organic bases or amino acids. Suitable inorganic cations are, for example, the lithium ion, the potassium ion, the calcium ion, the magnesium ion and especially the sodium ion. Suitable cations of organic bases are, among others, those of primary, secondary or tertiary amines, such as, for example, ethanolamine, diethanolamine, morpholine, glucamine, N,N-dimethylglucamine and especially N-methylglucamine. Suitable cations of amino acids are, for example, those of lysine, arginine and ornithine.

As proof for the above-named surprising and outstanding properties of the compounds according to the invention there are to be indicated the results of animal experimental studies to determine the acute intravenous ($LD_{50}$) as well as neural compatibility ($ED_{50}$) of two butyltriol compounds according to the invention, i.e., of compounds of general formula $I_A$ in comparison with the compound described in EP-A 0 255 471, which structurally is closest to the two butyltriol macrocycles:

1. Acute Toxicity Determination ($LD_{50}$)

In an individual cage (Rhema/Hofheim company) the contrast medium was administered to mice (weight: 18–22 g) approximately at body temperature in a caudal vein at a rate of 2 ml/min. Also preferred are those of 10-[2-hydroxy-2,2-bis(hydroxymethyl)ethyl]-1,4,7-triscarboxymethyl-1,4,7,10-tetraazacyclododecane, and 10-[1,1,1-tris(hydroxymethyl)methyl]-1,4,7-triscarboxymethyl-1,4,7,10-tetraazacyclododecane.

The contrast media were administered to 3 mice each in 3 doses at variable volumes and constant concentration. The allocation of the animals to the individual doses and the injection sequence of the doses took place by chance.

The observation period of the animals extended over 7 days per injection. The death of the animals was used as the criterion of the effectiveness.

2. Intracisternal Administration ($ED_{50}$)

The test substance was administered under light ether anesthesia to an equal number of female and male rats (130–170 g, Wistar-Han-Schering, SPF) once intracisternally by suboccipital puncture in constant volumes (0.08 ml/animal) in different concentrations (3 doses per 10 animals per substance). A volume sampling check (Ringer's solution) followed the study. Posture anomalies, spasms and death of the animals were evaluated as action criteria.

The statistical evaluation of all study results took place with the probit analysis.

3. Results

| Substance (Gd complex) | $R^2$ | Acute i.v. $LD_{50}$ (mmol/kg) | Neural $ED_{50}$ (micromol/kg) |
|---|---|---|---|
| Example 1 of this invention | —CH$_2$CH(OH)—CH(OH)CH$_2$OH | 35 | 27 |
| Example 2 of this invention | —CH(CH$_2$OH)—CH(OH)—CH$_2$OH | 30 | 29 |
| Example 6 EP-A 0255471 | —CH$_2$—CH(OH)—CH$_2$OH | 25 | 14 |

Contrast media for medical diagnosis should be eminently compatible and behave in as biologically inert manner as possible. Monomer contrast media should come as close as possible to the intravenous compatibility of, e.g., mannitol (i.e., 30–40 mmol/kg). Comparable compounds with lower values therefore are biologically not inert and show undesirable interaction with the organism. The propanediol derivative from EP-A 0 255 471 shows with an acute i.v. $LD_{50}$ of 25 mmol/kg clearly lower values than the two compounds according to the invention. This relevant difference indicates a certain chemotoxicity of the comparison substance. The undesirable interaction was shown particularly in the comparison of the test substances in the neural compatibility. The two compounds according to the invention showed a clearly better compatibility. With the propanediol compound already at doses of 14 micromol/kg changes in the behavior and marked spasms occurred. Some animals died at this dose.

With the macrocyclic gadolinium complexes of this invention a substantially better neural compatibility could be observed. A detrimental effect on behavior occurred only with doses approximately twice as high as with the comparison substance.

Conclusion

Since the two butyltriol compounds according to the invention also show a lower osmolality (0.59 or 0.57 in comparison with 0.62 osmol/kg; aqueous solutions of the Gd complexes in a concentration of 0.5 mol/l were measured) than the above-described propanediol compound, in summary it can be noted that the undesirable interactions of this compound with the biological organism surprisingly do not occur with the structurally closely related compounds according to the invention. The two butyltriol compounds show marked advantages and therefore are substantially more suitable as biologically inert contrast media.

The production of the compounds of general formula $I_A$ according to the invention takes place in that compounds of general formula II

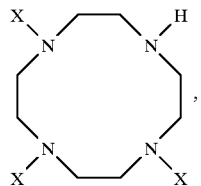

(II)

in which
X stands for a nitrogen protecting group or $CH_2COOY$ group with Y meaning hydrogen, an ammonium cation, an alkali metal or a protecting group,
are reacted with a substrate introducing the radical $R^2$ in protected form, the optionally contained nitrogen protecting groups X are removed and the —NH— groups thus released are alkylated with an acetic acid derivative of general formula III $HalCH_2COOY$ (III)

in which Hal stands for chlorine, bromine or iodine, the (hydroxy and optionally acid) protecting groups are removed and the resulting compounds of general formula $I_A$ with $R^1$ meaning hydrogen are converted with metal oxide or metal salt into the metal complexes of general formula $I_A$ with $R^1$ meaning a metal ion equivalent and then—if desired—still existing acidic hydrogen atoms are substituted by cations of inorganic and/or organic bases, amino acids or amino acid amides.

Suitable as acid protecting groups Y are lower alkyl, aryl and aralkyl groups, for example, the methyl, ethyl, propyl, n-butyl, t-butyl, phenyl, benzyl, diphenylmethyl, triphenylmethyl, bis(p-nitrophenyl)-methyl group as well as trialkylsilyl groups.

The acids $HalCH_2COOH$ can also be used in the form of their salts, preferably as Na or K salt.

The cleavage of the acid protecting groups takes place according to processes known to one skilled in the art, for example, by hydrolysis, hydrogenolysis, alkaline saponification of the esters with alkali in aqueous alcoholic solution at temperatures of 0 to 50° C., acid saponification with mineral acids or in case, e.g., of tert-butyl esters with the help of trifluoroacetic acid.

The three nitrogen atoms of feedstock II carry, before the reaction introducing the radical $R^2$, the group $CH_2COOY$ or nitrogen protecting groups, for example, the tosylate or trifluoroacetate group, which are cleaved according to methods known in the literature before the alkylation reaction that is to follow [the tosylates, e.g., with mineral acids, alkali metals in liquid ammonia, hydrobromic acid and phenol, RedAl$^{(R)}$, lithiumaluminum hydride, sodium amalgam, cf. e.g., Liebigs Ann. Chem. (1977), 1344, Tetrahedron Letters (1976), 3477; the trifluoracetates, e.g. with mineral acids or ammonia in methanol, cf.e.g., Tetrahedron Letters (1967), 289].

The N-alkylation with a haloacetic acid derivative of general formula III takes place in polar aprotic solvents such as, for example, dimethylformamide, dimethyl sulfoxide, acetonitrile, aqueous tetrahydrofuran or hexamethylphosphoric acid triamide in the presence of an acid trap such as, for example, tertiary amine (for example, triethylamine, trimethylamine, N,N-dimethylaminopyridine, 1,5-diazabicyclo[4.3.0]-nonene-5(DBN), 1,5-diazobicyclo [5.4.0]-undecene-5-(DBU), alkali, alkaline-earth carbonate, bicarbonate or hydroxide (for example, lithium, sodium, magnesium, calcium, barium, potassium carbonate, hydroxide and bicarbonate) at temperatures between –10° C. and 120° C., preferably between 0° C. and 50° C.

Suitable as hydroxy protecting groups are all those that can easily be introduced and later again be easily cleaved with re-formation of the finally desired free hydroxy group. Preferred protecting groups are ether groups such as, for example, the benzyl, 4-methoxybenzyl, 4-nitrobenzyl, trityl, di- and tri-phenylmethyl, trimethylsilyl, dimethyl-t-butylsilyl, diphenyl-t-butylsilyl group. But preferably the hydroxy groups are protected in the form of ketals, for example, with acetone, acetaldehyde, cyclohexanone or benzaldehyde.

The cleavage of the hydroxy protecting groups takes place in a way known in the art, for example, in case of a benzyl ether by reductive cleavage with lithium/ammonia or by hydrogenolytic cleavage in the presence, for example, of palladium-carbon and in case of a ether or ketal cleavage by acid treatment with the help, for example, of cation exchangers, trifluoroacetic acid or mineral acids [see, e.g., T. W. Greene "Protective Groups in Organic Synthesis," John Wiley and Sons (1981)].

The introduction of the radical $R^2$ takes place by alkylation of a substrate synthesized from a nucleofuge group for example Cl, Br, I, $CH_3C_6H_4SO_3$, $CF_3SO_3$, $CH_3SO_3$ and of the protected radical $R^2$ or of a substrate from which the desired radical $R^2$ is intramolecularly generated during the reaction. As an example for the last mentioned case there can be mentioned, the hydroxy epoxides 2,3-epoxy-1,4-dihydroxybutane and 1,2-epoxy-3,4-dihydroxybutane protected as, e.g., acetonides.

The reaction of feedstock II with X meaning a $CH_2COOY$ group is performed, e.g., in water, DMF, dioxane, alcohols, acetonitrile, tetrahydrofuran or their mixtures at temperatures of 0 to 100° C., preferably room temperature to 60° C., at a basic pH, preferably 9 to 13, within 6 hours to 2 days, preferably 12 to 36 hours.

If a macrocycle, protected on the residual nitrogen atoms, is used for the introduction of the $R^2$ radical in the reaction, the reaction takes place preferably in an autoclave in solvents such as, for example, DMF, DMA, toluene, methylene chloride or their mixtures at temperatures of 20 to 170° C., preferably 100 to 150° C., with addition of a base, such as, e.g., amines, alkali, alkaline-earth hydroxides and carbonates, preferably potassium and sodium carbonate and hydroxide, within 6 hours to 2 days, preferably 12 to 36 hours. If a substrate is used, which contains no nucleofuge group (i.e., for example, the above-mentioned epoxides), the use of a base can be dispensed with.

The compounds of general formula $I_A$ with $R^1$ meaning a hydrogen atom represent complexing agents. They can be isolated and purified or without isolation can be converted into metal complexes of general formula $I_a$ with at least two of substituents $R^1$ meaning a metal ion equivalent.

The production of the metal complexes according to the invention takes place in the way that was disclosed in German laid-open specification 34 01 052, by the metal oxide or a metal salt (for example, the nitrate, acetate, carbonate, chloride or sulfate of the element of the atomic numbers 21–29, 42, 44, 57–83) being dissolved or suspended in water and/or a lower alcohol (such as methanol, ethanol or isopropanol) and being reacted with the solution or suspension of the equivalent amount of the complexing ligand and then, if desired, by existing acidic hydrogen atoms being substituted by cations of inorganic and/or organic bases or amino acids.

The introduction of the desired metal ions take place both before and after cleavage of the hydroxy protecting groups.

The neutralization of possibly still existing free carboxy groups takes place with the help of inorganic bases (for example, hydroxides, carbonates or bicarbonates), for example, of sodium, potassium, lithium, magnesium or calcium and/or organic bases as, among others, primary, secondary and tertiary amines, such as, for example, ethanolamine, morpholine, glucamine, N-methyl and N,N-dimethylglucamine, as well as basic amino acids, such as, for example, lysine, arginine and ornithine or of amides of originally neutral or acidic amino acids.

For the production of neutral complex compounds so much of the desired bases is added to the acid complex salts in aqueous solution or suspension that the neutral point is reached. The resulting solution can then be evaporated to dryness in a vacuum. Often it is advantageous to precipitate the formed neutral salts by addition of water-miscible solvents, such as, for example, lower alcohols (methanol, ethanol, isopropanol and others), lower ketones (acetone and others), polar ethers (tetrahydrofuran, dioxane, 1,2-dimethoxyethane and others) and thus obtain crystallizates that are easy to isolate and purify. It has proved especially advantageous to add the desired base already during the complex formation of the reaction mixture and thus to save a process step.

Another possibility to achieve neutral complex compounds consists in converting the remaining acid groups in the complex entirely or partially, for example, to esters or amides. This can occur by subsequent reaction on the finished complex (e.g., by exhaustive reaction of the free carboxy groups with dimethyl sulfate.

The production of the pharmaceutical agents according to the invention also takes place in a way known in the art, by complex compounds according to the invention—optionally by addition of additives usual in galenicals—being suspended or dissolved in aqueous medium and then the suspension or solution optionally being sterilized. Suitable additives are, for example, physiologically safe buffers (such as, for example, tromethamine), additives of complexing agents (such as, for example, diethylenetriaminepentaacetic acid) or—if desired—electrolytes, such as, for example, sodium, calcium, magnesium, zinc chlorides, phosphates and citrates or—if necessary—antioxidizing agents, such as, for example, ascorbic acid.

If suspensions or solutions of agents according to the invention in water or physiological salt solution are desired for enteral administration or other purposes, they are mixed with one or more auxiliary agents usual in galenicals (for example, methylcellulose, lactose, mannitol) and/or surfactants (for example, lecithins, Tween(R), Myrj(R)) and/or aromatic substance(s) for taste correction (for example, essential oils).

In principle it is also possible to produce pharmaceutical agents according to the invention even without isolation of complex salts. In any case, special care must be used to perform the chelate formation so that the salts and salt solutions according to the invention are produced practically free of uncomplexed toxically acting metal ions.

This can be guaranteed, for example with the help of color indicators such as xylenol orange by control filtrations during the production process. The invention therefore relates also to processes for the production of complex compounds and their salts. A purification of the isolated complex salt remains as final safety measure.

The pharmaceutical agents according to the invention preferably contain 0.1 micromol-3 mol/l of the complex salt and generally are dosed in amounts of 0.1 micromol-5 mmol/kg. They are intended for enteral and parenteral administration. The complex compounds according to the invention can be used:

1. for NMR and x-ray diagnosis in the form of their complexes with the ions of elements without atomic numbers 21–29, 42, 44 and 57–83;
2. for radiodiagnosis and radiotherapy in the form of their complexes with the radioisotopes of the elements with atomic numbers 27, 29, 31, 32, 37–39, 43, 49, 62, 64, 70, 75 and 77.

The agents according to the invention meet the varied requirements for the suitability as contrast media for nuclear spin tomography. Thus they are outstandingly suitable for improving, in its expressive power, the image obtained with the nuclear spin tomograph, by enhancing the signal intensity after enteral or parenteral administration. Further, they show the great effectiveness, which is necessary, to load the body with the smallest possible amounts of foreign substances, and the good compatibility, which is necessary to maintain the noninvasive character of the examinations.

The good water solubility and low osmolality of the agents according to the invention make it possible to produce highly concentrated solutions, to maintain the volume load of the circulation in justifiable limits and to balance the dilution by the body fluid, i.e., NMR diagnostic media have to be 100 to 1000 times better water soluble than for NMR spectroscopy. Further, the agents according to the invention exhibit not only a great stability in vitro but also a surprisingly great stability in vivo so that a release or an exchange of the ions, not covalently bound in the complexes—toxic in themselves—within the time, in which the new contrast media again are completely excreted now takes place extremely slowly.

In general, the agents according to the invention for use as NMR diagnostic media was dosed in amounts of 0.0001–5 mmol/kg, preferably 0.005–05 mmol/kg. Details of the use are discussed, for example, in H. J. Weinmann et al., Am. J. of Roentgenology 142, 619 (1984).

Further, the complex compounds according to the invention can advantageously be used as susceptibility reagents and shift reagents for the in vivo NMR spectroscopy.

Because of their favorable radioactive properties and of the good stability of the complex compounds contained in them, the agents according to the invention are also suitable as radiodiagnostic media. Details of their use and dosage are described, e.g., in "Radiotracers for Medical Applications," CRC Press, Boca Raton, Fla.

Another imaging method with radioisotopes is positron emission tomography, which uses positron-emitting isotopes such as, for example, $^{43}$Sc, $^{44}$Sc, $^{52}$Fe, $^{55}$Co and $^{68}$Ga (Heiss, W. D.; Phelps, M. E.; Positron Emission Tomography of Brain, Springer Verlag Berlin, Heidelberg, New York 1983).

The compounds according to the invention can also be used in radioimmuno or radiation therapy. It differs from the corresponding diagnosis only by the amount and type of isotope used. In this case, the aim is to destroy tumor cells by energy-rich shortwave radiation with a smallest possible range. Suitable beta-emitting ions are, for example, $^{46}$Sc, $^{47}$Sc, $^{48}$Sc, $^{72}$Ga, $^{73}$Ga and $^{90}$Y. Suitable alpha-emitting ions exhibiting a short life are, for example, $^{211}$Bi, $^{212}$Bi, $^{213}$Bi and $^{214}$Bi, and $^{212}$Bi is preferred. A suitable photon- and electron-emitting ion is $^{158}$Gd, which can be obtained from $^{157}$Gd by neutron capture.

If the agent according to the invention is intended for the use in the variant of radiation therapy proposed by R. L. Mills et al. [Nature Vol. 336 (1988), p. 787], the central ion has to be derived from a Moessbauer isotope such as, for example, $^{57}$Fe or $^{151}$Eu.

In the in vivo application of the therapeutic agents according to the invention, they can be administered together with a suitable carrier such as, for example, serum or physiological common salt solution and together with another protein such as, for example, human serum albumin. In this case, the dosage depends on type of cellular impairment, the metal ion used and the type of method, e.g., brachytherapy.

The therapeutic agents according to the invention are administered parenterally.

Details of the use of radiotherapeutic agents are discussed, e.g., in R. W. Kozak et al. TIBTEC, October 1986, 262.

The agents according to the invention, because of their outstanding water solubility and because of the low osmotic pressure of their concentrated aqueous solutions, are excellent x-ray contrast media, and it is to be especially emphasized that with them in biochemical-pharmacological studies no indications can be perceived of the known anaphylactic-type reactions from the iodine-containing contrast media. Because of the favorable absorption properties in the ranges of higher tube voltages they are especially valuable for digital subtraction techniques.

In general, the agents according to the invention for use as x-ray contrast media are dosed analogously to, e.g., meglumine diatrizoate in amounts of 0.1–5 mmol/kg, preferably 0.25–1 mmol/kg.

Details of the use of x-ray contrast media are discussed, for example, in Barke, Roentgenkontrastmittel [X-ray Contrast Media], G. Thieme, Leipzig (1970) and P. Thurn, E. Buecheler—Einfuehrung in die Roentgendiagnostik [Introduction to X-ray Diagnosis], G. Thieme, Stuttgart, New York (1977).

Altogether it has been possible to synthesize new complexing agents, metal complexes and metal complex salts, which open up new possibilities in diagnostic and therapeutic medicine. Especially the development of novel imaging processes in medical diagnosis makes this development appear desirable.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 40 09 119.8 are hereby incorporated by reference.

The purpose of following examples is to provide a more detailed explanation of the object of the invention.

EXAMPLE 1 a) 10-(2,3,4-Trihydroxybutyl)-1,4,7-triscarboxymethyl-1,4,7,10-tetraazacyclododecane 10.0 g (28.87 mmol) of 1,4,7-triscarboxymethyl-1,4,7,10-tetraazacyclododecane (DO3A) is dissolved in 40 ml water and the pH is adjusted to 13 with 5 normal sodium hydroxide solution. A solution of 6.24 g (43.30 mmol) of 2-(2,2-dimethyl-1,3-dioxolan-4-yl)-ethylene oxide (DE 3 150 917) in 10 ml of dioxane is added and stirred for 24 hours at room temperature. It is diluted with 60 ml of water and extracted three times with 50 ml of ether. The aqueous phase is brought to pH 2 with 10% hydrochloric acid and concentrated by evaporation. The residue is dissolved in some water and poured on a cation exchange column (IR 120). After rinsing with water, the ligand is eluted with 0.5 normal aqueous ammonia solution. The fractions are concentrated by evaporation, the ammonium salt is taken up with a little water and poured over an anion exchange column (IRA 67). It is first washed with water and then eluted with 0.5 normal aqueous formic acid.

It is concentrated by evaporation in a vacuum, the residue is dissolved in a little hot methanol and acetone is added, and the title compound is crystallized out.

11.31 g (87% of theory) of white powder is obtained, which dissolves in the air (according to analysis 11.1% water).

Analysis: (corrected for water); Cld: C 47.99 H 7.61 N 12.44 O 31.97; Fnd: C 47.93 H 7.67 N 12.40 b) Gadolinium complex of 10-(2,3,4-trihydroxybutyl)-1,4,7-triscarboxymethyl-1,4,7,10-tetraazacyclododecane 10.0 g (22.2 mmol) of the compound obtained according to 1a) is dissolved in 60 ml of deionized water and 4.02 g (11.1 mmol) of gadolinium oxide is added. It is heated to 90° C. for 3 hours.

The cooled solution is stirred with 2 ml each of acid ion exchanger (IR 120) and 2 ml of basic exchanger (IRA 410) for 1 hour at room temperature. It is filtered from the exchanger and the filtrate is briefly boiled with activated carbon.

After filtering and freeze-drying, 12.76 g (95% of theory) of a white amorphous powder is obtained (12.3% water according to analysis).

Analysis: (corrected for water); Cld: C 35.73 H 5.17 N 9.26 O 23.8 Gd 25.99; Fnd: C 35.68 H 5.24 N 9.21 Gd 25.93

EXAMPLE 2 a) 10-(6-Hydroxy-2,2-dimethyl-1,3-dioxepan-5-yl)-1,4,7-tris(p-toluenesulfonyl)-1,4,7,10-tetraazacyclododecane 50 g (78.76 mmol) of 4,7,10-tris(p-toluenesulfonyl)-1,4,7,10-tetraazacyclododecane and 13.63 g (94.51 mmol) of 4,4-dimethyl-3,5,8-trioxabicyclo-[5.1.0]-octane are dissolved in 300 ml of dimethylformamide and heated in an autoclave for 24 hours to 170° C. It is evaporated to dryness and the residue is chromatographed on silica gel (mobile solvent: methylene chloride/hexane/acetone: 10/5/1). The main fractions are concentrated by evaporation and recrystallized from methyl tert-butyl ether/methanol. Yield: 52.76 g (86% of theory) of a cream-colored powder.

Analysis: Cld: C 55.51 H 6.47 N 7.19 S 12.35; Fnd: C 55.46 H 6.52 N 7.18 S 12.32 b) 10-(6-Hydroxy-2,2-dimethyl-1,3-dioxepan-5-yl)-1,4,7-tetraazacyclododecane 50 g (64.19 mmol) of the title compound from example 2a) is suspended in 800 ml of liquid ammonia/400 ml of tetrahydrofuran and cooled to −35° C. 8.9 g (1.28 mol) of lithium is added within 30 minutes and stirred at −35° C. for 8 hours. The excess lithium is destroyed by careful addition of methanol. The ammonia gas is carefully allowed to evaporate and then evaporated to dryness. The residue is taken up with 200 ml of 4 normal sodium hydroxide solution and extracted three times with 400 ml of hot toluene. The organic phases are dried on potassium hydroxide pellets and then concentrated by evaporation in a vacuum. The remaining oil is chromatographed (mobile solvent: methanol/water/conc. ammonia solution=10/1/1). 8.53 g (42% of theory) of a light yellow oil is obtained, which solidifies when left standing.

(8.1% water according to analysis). Analysis: (corrected for water): Cld: C 56.93 H 10.19 N 17.71; Fnd: C 56.88 H 10.15 N 17.64 c) 10-(1-Hydroxymethyl-2,3-dihydroxypropyl)-1,4,7-triscarboxymethyl-1,4,7,10-tetraazacyclododecane 8 g (25.28 mmol) of the title compound from example 2b) is dissolved in 50 ml of water and 14.05 g (101.12 mmol) of bromoacetic acid is added. The pH is brought to 9.5 with 6 normal potassium hydroxide solution.

It is heated to 50° C. and the pH is kept between 9.5–10 by addition of 6 n potassium hydroxide solution. After 12 hours of stirring at 50° C. it is cooled in an ice bath, adjusted to pH 2 with concentrated hydrochloric acid and evaporated to dryness in a vacuum.

The residue is dissolved in a little water and poured onto a cation exchange column (IR 120). After rinsing with water, the ligand is eluted with 0.5 normal aqueous ammonia solution. The fractions are concentrated by evaporation, the ammonium salt is taken up with a little water and poured onto an anion exchange column (IRA 67). It is washed first with water and then eluted with 0.5 normal aqueous formic acid. It is concentrated by evaporation in a vacuum, the residue is dissolved in a little hot methanol and acetone is added. After cooling in an ice bath, the title compound is crystallized out.

Yield: 8.56 g (69% of theory) of a hygroscopic solid, 9.1% of water according to analysis). Analysis: (corrected for water): Cld: C 51.42 H 7.81 N 11.42; Fnd: C 51.37 H 7.86 N 11.37 d) Gadolinium complex of 10-(1-hydroxymethyl-2,3-dihydroxypropyl)-1,4,7-triscarboxymethyl-1,4,7,10-tetraazacyclododecane 8 g (16.31 mmol) of the title compound from example 2c) is dissolved in 50 ml of deionized water and 2.96 g (8.15 mmol) of gadolinium oxide is added. It is heated for 3 hours to 90° C. The cooled solution is stirred with 2 ml each of acidic ion exchanger (IR 120) and 2 ml of basic exchanger (IRA 410) for 1 hour at room temperature. The exchanger is filtered off and the filtrate is briefly boiled with activated carbon. After filtration and freeze-drying, 9.99 g (95% of theory) of an amorphous powder (7.8% of water according to analysis) is obtained.

Analysis: (corrected for water): Cld: C 39.12 H 5.47 N 8.69 Gd 24.39; Fnd: C 39.07 H 5.51 N 8.61 Cd 24.32

EXAMPLE 3

Dysprosium complex of 10-(2,3-4-trihydroxybutyl)1,4,7-triscarboxymethyl-1,4,7,10-tetraazacyclododecane Analogously to the instructions of 1b) the desired dysprosium complex is obtained by starting from 1a) with dysprosium oxide instead of gadolinium oxide.

Analysis: (corrected for water): Cld: C 35.44 H 5.12 N 9.19 Dy 26.64; Fnd: C 35.38 H 5.19 N 9.13 Dy 26.59

EXAMPLE 4

Bismuth complex of 10-(2,3-4-trihydroxybutyl)1,4,7-triscarboxymethyl-1,4,7,10-tetraazacyclododecane Analogously to the instructions of 1b) the corresponding bismuth complex is obtained by starting from 1a) with bismuth oxide instead of gadolinium oxide.

Analysis: (corrected for water): Cld: C 32.93 H 4.76 N 8.54 Bi 31.84; Fnd: C 32.87 H 4.81 N 8.49 Bi 31.78

EXAMPLE 5

Ytterbium complex of 10-(1-hydroxymethyl-2,3-dihydroxypropyl)-1,4,7-triscarboxymethyl-1,4,7,10-tetraazacyclododecane Analogously to the instructions of 2d) the corresponding ytterbium complex is obtained by starting from 2c) with ytterbium oxide instead of gadolinium oxide.

Analysis: (corrected for water): Cld: C 34.84 H 5.04 N 9.03 Yb 27.89; Fnd: C 34.79 H 5.10 N 9.01 Yb 27.83

EXAMPLE 6

Lutetium complex of 10-(1-hydroxymethyl-2,3-dihydroxypropyl)-1,4,7-triscarboxymethyl-1,4,7,10-tetraazacyclododecane Analogously to the instructions of 2d) the corresponding lutetium complex is obtained by starting from 2c) with lutetium oxide instead of gadolinium oxide.

Analysis: (corrected for water): Cld: C 34.73 H 5.02 N 9.00 Lu 28.11; Fnd: C 34.67 H 4.96 N 8.96 Lu 28.06

EXAMPLE 7

Europium $^{151}$ complex of 10-(1-hydroxymethyl-2,3-dihydroxypropyl)-1,4,7-triscarboxymethyl-1,4,7,10-tetraazacyclododecane Analogously to the instructions of 2d) the corresponding europium$^{151}$ complex is obtained by starting from 2c) with europium oxide ($^{151}Eu_2O_3$) instead of gadolinium oxide.

Analysis: (corrected for water): Cld: C 36.06 H 5.21 N 9.35 Eu 25.35; Fnd: C 36.01 H 5.29 N 9.30 Eu 25.29

EXAMPLE 8

Manganese(II) complex of 10-(1-hydroxymethyl-2,3-dihydroxypropyl)-1,4,7-triscarboxymethyl-1,4,7,10-tetraazacyclododecane as sodium salt 10 g (22.2 mmol) of the title compound from example 2c) is dissolved in 80 ml of deionized water and 2.55 g (22.2 mmol) of manganese(II) carbonate is added. It is heated for 3 hours to 90° C.

The cooled solution is stirred for 1 hour with 10 ml of weakly acidic ion exchanger (AMB 252c) at room temperature. It is filtered off from the exchanger. The filtrate is adjusted to pH 7.2 with 2N sodium hydroxide solution and freeze-dried.

Yield: 10.75 g (93% of theory) of a colorless amorphous powder.

(6.3% of water according to analysis). Analysis: (corrected for water): Cld: C 41.15 H 5.95 N 10.66 Mn 10.46 Na 4.38; Fnd: C 41.08 H 6.03 N 10.58 Mn 10.41 Na 4.43

EXAMPLE 9

Production of a solution of indium-111 complex of 10-(1-hydroxymethyl-2,3-dihydroxypropyl)-1,4,7-triscarboxymethyl-1,4,7,10-tetraazacyclododecane A solution of 100 micrograms of the complexing agent, described in example 2c), in 5 ml of a mixture of 150 mmolar common salt solution and 150 mmolar sodium acetate solution (pH 5.8) is mixed with 4.5 ml of indium-111 chloride solution (0.01 mmolar) in 1 ml of 0.15 n hydrochloric acid and heated for 1 hour to 80° C. Then the solution is brought to a pH of 7.2 by addition of 0.1 n sodium hydroxide solution. The solution was sterilized by filtration and freeze-dried. The residue is taken up in physiological common salt solution and then represents a preparation suitable for radiodiagnosis.

EXAMPLE 10

Production of a solution of gadolinium complex of 1-(1-hydroxymethyl-2,3-dihydroxypropyl)-4,7,10-triscarboxymethyl-1,4,7,10-tetraazacyclododecane 322.39 g (=0.5 mol) of the compound described in example 2d) is dissolved in 600 ml of water pro injectione (p.i.). After addition of 1.5 g of monohydrate of the calcium trisodium salt of DPTA, CaNa₃DPTA and 1.21 g of trishydroxymethylaminomethane a pH of 7.0 is adjusted with dilute hydrochloric acid and water p.i. is added to produce 1000 ml. The solution is ultrafiltered, poured into bottles and heat-sterilized.

EXAMPLE 11

Production of a solution of the yttrium-90 complex of 1-(1-hydroxymethyl-2,3-dihydroxypropyl)-4,7,10-triscarboxymethyl-1,4,7,10-tetraazacyclododecane 5 microliters of a Y-90 solution (2 microcuries) is added to a solution of 10 micromol of the compound described in example 2d) in 90 microliters ammonium acetate buffer (pH 6.0) and the mixture is incubated for 30 minutes at 37° C. 10 micromol of calcium trisodium salt of DTPA is added and, after ultrafiltration a preparation suitable for radiotherapy is obtained.

EXAMPLE 12

Production of a solution of the gadolinium complex of 10-2,3,4-trihydroxybutyl)-1,4,7-triscarboxymethyl-1,4,7,10-tetraazacyclododecane 967.5 g of the complex described in example 1b) is suspended in 500 ml of bidistilled water. It is brought to pH 7.3 by addition of 1.89 g of sodium bicarbonate, 162.3 mg of CaNa₂EDTA is added and with heating bidistilled water is added to make a volume of 1 liter. After filtration through a pore size of 0.22 microns, the solution is poured into Multivials and sterilized for 20 minutes at 120° C. A contrast medium for x-ray diagnosis is obtained.

EXAMPLE 13

Example for an NMR-diagnostic in vivo examination:

Demonstration of a cerebral infarction in the rat by the gadolinium complex of 10-(1-hydroxymethyl-2,3-dihydroxypropyl)-1,4,7-tris-carboxymethyl-1,4,7,10-tetraazacyclododecane (example 2d) with a dose of 0.1 and 0.3 mmol of Gd/kg The experimental animal was a female Wistar rat weighing 200 g. For the induction of the cerebral infarction, the animal was first anesthetized. After intravenous injection of Bengal red with a dose of 20 mg/kg, an area of the brain about 0.7 cm in diameter near the bregma point was irradiated through the cranium with light of wavelength 548 nm (this corresponds to the maximum absorption of Bengal red), by which, because of the formation of singlet oxygen by a chain of various reactions, there results the aggregation of platelets and thus an infarction in the irradiated region.

The imaging took place in an MRI experimental device of the General Electric company (field strength, 2 teslas). It was performed with a spin echo sequence (TR=400 msec, Ts=20 msec). The layer thickness was 3 mm, and 4 averagings were performed respectively.

An axial sectional plane image without contrast medium where the cranium points downward was taken, The infarction area is indicated only quite weakly by a lower sight intensity in comparison to the healthy tissue. In an image of the same rat in the same sectional plane, a clear enhancement (clearly increased signal intensity) in the area of infarction and the distance of the blood-brain barrier connected with it can be seen in an image taken 1 minute after administration of the contrast medium (0.1 mmol of Gd/kg). The same animal was administered another dose after about 20 minutes, this time in the amount of 0.3 mmol of Gd/kg. In an image along the same sectional plane, an enhancement substantially stronger than after the smaller dose is shown clearly 1 minute after the administration; moreover the infarction area can be better defined.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,4,7,10-tetraazacyclododecane butyltriol of formula $I_A$

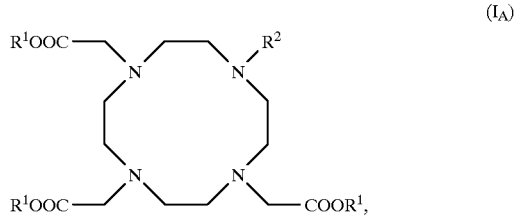

in which
each $R_1$ is hydrogen or a metal ion equivalent, independent of one another, and
$R_2$ is 1-hydroxymethyl-2,3-dihydroxypropyl, or a salt thereof with an organic or inorganic base or an amino acid.

2. A compound according to claim 1, wherein all $R^1$'s are hydrogen atoms.

3. A compound according to claim 1, wherein at least two of substituents $R^1$ are metal ion equivalents of at least one element of the atomic numbers 21–29, 42, 44 or 57–83 or at least one radionuclide of an element of the atomic numbers 27, 29, 31, 32, 37–39, 43, 49, 62, 64, 70 or 77.

4. 10-(1-hydroxymethyl-2,3-dihydroxypropyl)-1,4,7-triscarboxymethyl-1,4,7,10-tetraazacyclododecane, a compound of claim 1.

5. A compound of claim 1, wherein said metal ion equivalents are of at least one element of atomic numbers 21–29, 42, 44 or 58–70.

6. A pharmaceutical composition comprising a compound of claim 1 and a pharmaceutically acceptable carrier.

7. A method of conducting NMR imaging comprising administering a composition of claim 6 effective therefor.

8. A pharmaceutical composition comprising a compound of claim 3 and a pharmaceutically acceptable carrier.

9. A method of conducting NMR imaging comprising administering a composition of claim 8.

10. The gadolinium (III) complex of 10-(1-hydroxymethyl-2,3-dihydroxypropyl)-1,4,7-triscarboxymethyl-1,4,7,10-tetraazacyclododecane.

11. A pharmaceutical composition comprising a compound of claim 10 and a pharmaceutically acceptable carrier.

12. A method of conducting NMR imaging comprising administering a composition of claim 11.

* * * * *